United States Patent [19]

Zahir et al.

[11] Patent Number: 5,262,501
[45] Date of Patent: Nov. 16, 1993

[54] MIXTURES OF SPIROHEPTADIENES

[75] Inventors: Sheik Abdul-Cader Zahir, Oberwil, Switzerland; Cécile Pasquier, Semsales, both of Switzerland; Wolfgang Scharf, Grenzach-Wyhlen, Fed. Rep. of Germany; Maurice Dupré, Marly, Switzerland

[73] Assignee: Ciga-Geigy Corporation, Ardsley, N.Y.

[21] Appl. No.: 881,587

[22] Filed: May 12, 1992

[30] Foreign Application Priority Data

May 17, 1991 [CH] Switzerland ............... 1476/91
Jul. 15, 1991 [CH] Switzerland ............... 2096/91

[51] Int. Cl.⁵ ................ C08F 32/08; C07C 13/28
[52] U.S. Cl. ..................... 526/283; 585/21; 585/22; 585/23
[58] Field of Search ........................ 526/283

[56] References Cited

U.S. PATENT DOCUMENTS 2,726,232 12/1955 Upson .................. 260/93.1
4,140,843 2/1979 Widmer et al. ............ 528/392

FOREIGN PATENT DOCUMENTS 1643855 2/1975 Fed. Rep. of Germany .

Primary Examiner—Jospeh L. Schofer
Assistant Examiner—Wu C. Cheng
Attorney, Agent, or Firm—William A. Teoli, Jr.

[57] ABSTRACT

Mixtures essentially comprising compounds of formula I or II

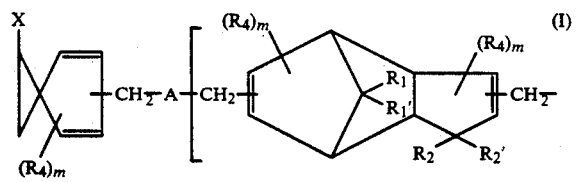

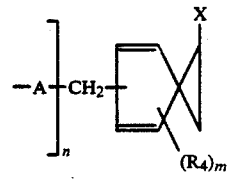

or

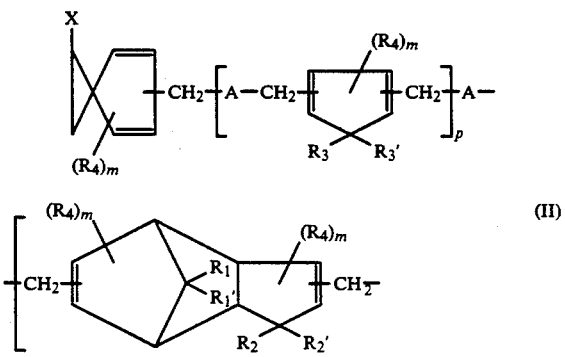

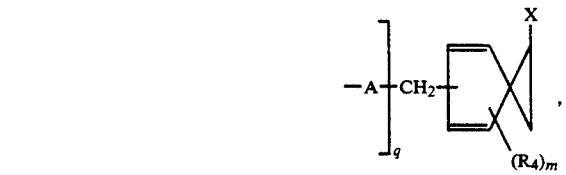

wherein X is a hydrogen atom or vinyl, A is a divalent aromatic radical which is unsubstituted or substituted by one or more $C_1$–$C_{20}$alkyl groups, halogen atoms or halogen-substituted $C_1$–$C_{20}$alkyl groups, $R_1$, $R_1'$, $R_2$, $R_2'$, $R_3$ and $R_3'$ are each a hydrogen atom, or $R_1$ and $R_1'$, $R_2$ and $R_2'$ and $R_3$ and $R_3'$ are each together ethylene, $R_4$ is $C_1$–$C_6$alkyl, phenylalkyl containing 1 to 6 carbon atoms in the alkyl moiety or is trialkylsilyl containing 1 to 6 carbon atoms in each alkyl moiety, m is 0, 1 or 2, n is 0 or an average number from 1 to 200, p is an average number from 1 to 100 and q is 0 or an average number from 1 to 100, can be cured by heating and are suitable for making laminates, especially for fabricating copper-clad circuit boards.

8 Claims, No Drawings

MIXTURES OF SPIROHEPTADIENES

The present invention relates to mixtures of novel spiro[2,4]hepta-4,6-dienes based on aromatic bis(-halomethyl) compounds, to their preparation and to the use thereof, especially as laminating resins.

Dimeric and oligomeric cyclopentadienes based on aromatic bis(chloromethyl) compounds are known. For example, unsubstituted and substituted, dimeric and oligomeric cyclopentadienes based on aromatic bis(cyclopentadienyl)xylenes and the use thereof, inter alia as laminating resins, are disclosed in U.S. Pat. No. 2,726,232 and in DE-Auslegeschrift 16 43 855. These known resins have only poor storage stability, so that the prepregs made from them have to be processed immediately to mouldings.

It has now been found that reaction of the known aromatic bis(cyclopentadienyl) compounds with 1,2-dichloroethane or 1,2-dibromoethane gives novel spiro[2,4]hepta-4,6-dienes which, compared with the prior art resins, have improved storage stability, in particular improved resistance to oxidation, and hence are distinguished by better processing properties, especially for the production of laminates and compression mouldings. The cured spiro[2,4]hepta-4,6-dienes advantageously have a dielectric constant of below 3, so that they are particularly suitable for use as laminating resins for the fabrication of printed circuits which are used in high frequency electrical engineering.

Accordingly, the invention relates to mixtures essentially comprising compounds of formula I or II

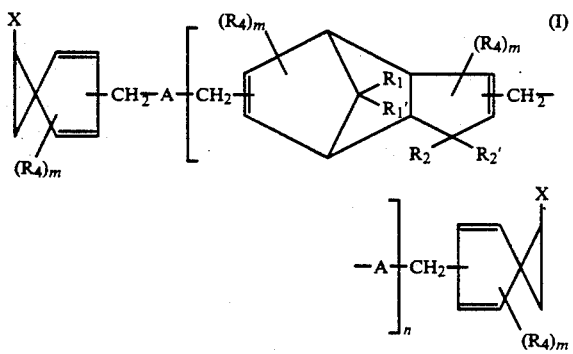

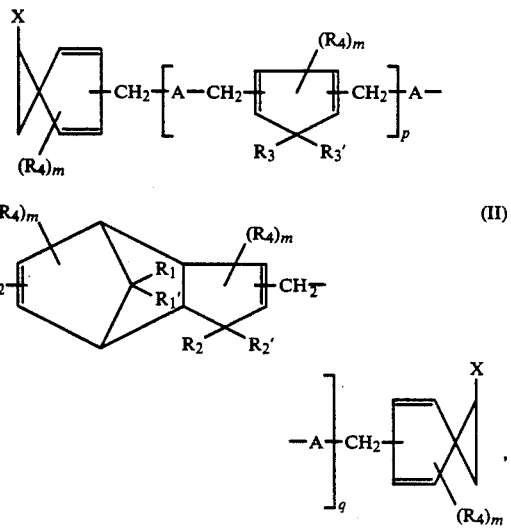

wherein X is a hydrogen atom or vinyl, A is a divalent aromatic radical which is unsubstituted or substituted by one or more $C_1$–$C_{20}$alkyl groups, halogen atoms or halogen-substituted $C_1$–$C_{20}$alkyl groups, $R_1$, $R_1'$, $R_2$, $R_2'$, $R_3$ and $R_3'$ are each a hydrogen atom, or $R_1$ and $R_1'$, $R_2$ and $R_2'$ and $R_3$ and $R_3'$ are each together ethylene, $R_4$ is $C_1$–$C_6$alkyl, phenylalkyl containing 1 to 6 carbon atoms in the alkyl moiety or is trialkylsilyl containing 1 to 6 carbon atoms in each alkyl moiety, m is 0, 1 or 2, n is 0 or an average number from 1 to 200, p is an average number from 1 to 100 and q is 0 or an average number from 1 to 100.

X in formulae I and II is preferably a hydrogen atom.

In particular, the novel mixtures comprise essentially compounds of formula I, wherein A, $R_1$, $R_1'$, $R_2$, $R_2'$, $R_4$, m and n are as previously defined.

The divalent aromatic radical A in the novel mixtures of formulae I and II may be a radical containing one or more benzene nuclei, which benzene nuclei may be fused or linked to each other through a direct bond or through linking groups, and wherein the aromatic rings may carry the same or different substituents.

A may typically be a radical of the following formulae:

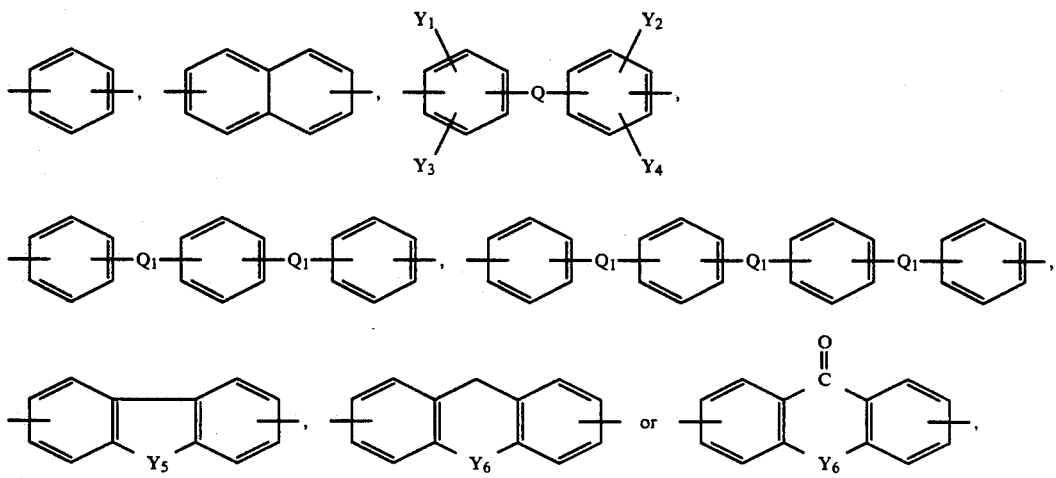

wherein Q is a direct bond, —CH$_2$)$_r$, —CH$_2$CH$_2$—, —CH(CH$_3$)—, —C(CH$_3$)$_2$—, —C(CF$_3$)—, —O—, —S—, —SO$_2$—, or —CO—, where r is a number from 1 to 12, Q$_1$ is a direct bond, —CH$_2$—, —CH$_2$—CH$_2$, —CH(CH$_3$)—, —C—(CF$_3$)—, —O—, —S—, —SO$_2$— or —CO—, n is 2-12, Y$_1$, Y$_2$, Y$_3$ and Y$_4$ are each independently of one another a hydrogen atom, a halogen atom or C$_1$-C$_4$alkyl, Y$_5$ is —CH$_2$—, —O—, —S—, —NH— or —CO— and Y$_6$ is —CH$_2$—, —O—, —S— or —NH—.

fined, m is 0, 1 or 2, and R$_4$ is methyl or ethyl, and n is 0 or an average number from 1 to 20.

More particularly, the novel mixtures comprise compounds of formula I or II, wherein A is phenylene or biphenylene, R$_1$, R$_1'$, R$_2$ and R$_2'$ are as previously defined, and n is 0 or an average number from 1 to 20, preferably from 1 to 10.

The novel mixtures comprising compounds of formula I or II may conveniently be prepared by reacting compounds of formula III or IV

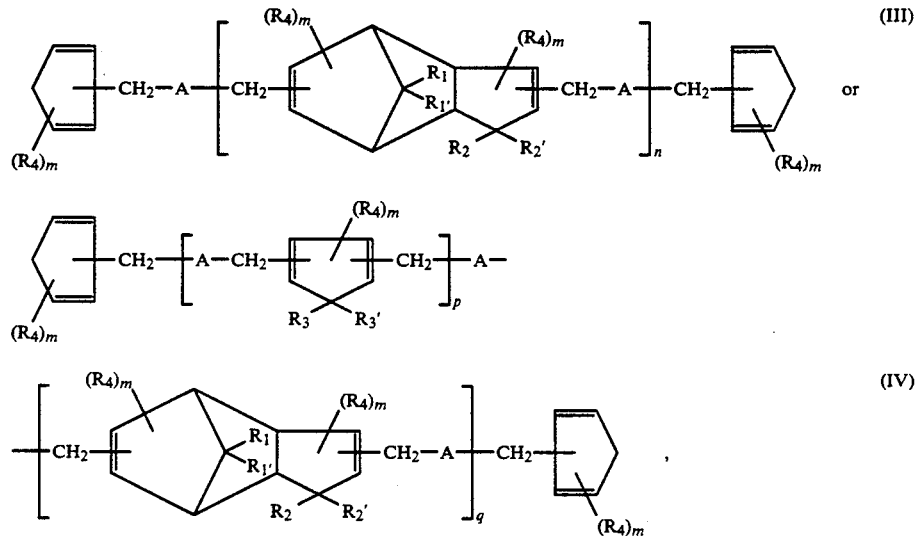

The C$_1$-C$_{20}$alkyl groups as substituents of the aromatic radical A and the C$_1$-C$_6$alkyl groups as substituents R$_4$ may be linear or branched. Such groups are typically methyl, ethyl, n-propyl, isopropyl, n-butyl, tert-butyl, n-pentyl, isopentyl, neopentyl, 2,2-dimethylpentyl, 2-methylhexyl, 2,2,3-trimethylbutyl, isooctyl and dodecyl.

Fluoro, chloro, bromo or iodo as halogen may be substituted at the aromatic ring. Preferably fluoro or chloro as halogen are substituted at the aromatic rings.

Halogen-substituted C$_1$-C$_{20}$alkyl groups may suitably be chloromethyl, 2-bromoethyl, 3-chloro-n-propyl, chloroisopropyl or 5-chloro-n-pentyl and, preferably, perfluoralkyl groups.

Suitable phenylalkyl groups may be phenylethyl or phenylpropyl and, preferably, benzyl.

Trialkylsilyl is preferably trimethylsilyl or triethylsilyl.

The novel mixtures preferably comprise compounds of formula I or II, wherein A is an unsubstituted or a C$_1$-C$_4$-alkyl-substituted radical of formula

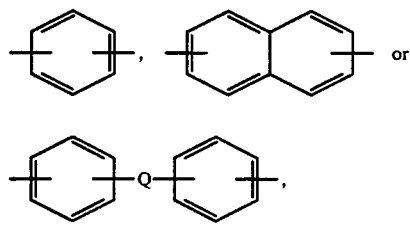

wherein Q is a direct bond, —CH$_2$)$_r$, —C(CH$_3$)$_2$—, —O, —CO—, —S— or —SO$_2$—, where r is a number from 1 to 12, R$_1$, R$_1'$, R$_2$ and R$_2'$ are as previously dewherein A, R$_1$, R$_1'$, R$_2$, R$_2'$, R$_3$, R$_3'$, R$_4$, m, n, p and q are as previously defined, with 1,2-dichloroethane, 1,2-dibromoethane, 1,4-dichloro- or 1,4-dibromobut-2-ene in the presence of a phase transfer catalyst and of alkali in the temperature range from 20° to 50° C., using at least 0.1 mol of 1,2-dichloroethane, 1,2-dibromoethane, 1,4-dichloro- or 1,4-dibromobut-2-ene per 1 mol of compound of formula III or IV.

It is preferred to use in this process at least 2 mol, usually 2 to 10 mol, of 1,2-dichloroethane, 1,2-dibromoethane, 1,4-dichloro- or 1,4-dibromobut-2-ene per 1 mol of compound of formula III or IV.

Compounds of formula III, wherein R$_1$, R$_1'$, R$_2$ and R$_2'$ are each a hydrogen atom, are known, inter alia from U.S. Pat. No. 2,726,232 or from DE-Auslegeschrift 1 643 855, and can be prepared by reacting 1 mol of a compound of formula V $$X—CH_2—A—CH_2—X \qquad (V),$$

wherein X is halogen, preferably chloro or bromo, or is the radical —OSO$_2$—R, where R is C$_1$-C$_4$alkyl, with 2 mol of cyclopentadiene in the presence of a phase transfer catalyst and aqueous sodium hydroxide, in the temperature range from 25° to 50° C., to give initially compounds of formula III, wherein n is 0, which can then be polymerised by heating to c. 50°-100° C. by a Diels-Alder reaction to compounds of formula III, wherein n is an integer from 1 to 200.

The compounds of formula III, wherein R$_1$ and R$_1'$ as well as R$_2$ and R$_2'$ are also each together ethylene, R$_4$, m and A are as previously defined and n is an average number from 1 to 200, have not yet been described in the literature and can be prepared by a Diels-Alder reaction of compounds of formula I with compounds of formula III, wherein n is 0, at elevated temperature, typically from 50° to 100° C. Such reaction mixtures are usually obtained by using for the preparation of compounds of formula I, wherein n is 0, the 1,2-dichloroethane, 1,2-dibromoethane, 1,4-dichloro- or 1,4-dibromobut-2-ene in less than required amounts i.e. using per mol of compound of formula III, wherein n is 0, less than 2 mol of 1,2-dichloroethane, 1,2-dibromoethane, 1,4-dichloro- or 1,4-dibromobut-2-ene.

The invention accordingly also relates to mixtures of compounds of formula III, wherein $R_1$ and $R_1'$ as well as $R_2$ and $R_2'$ are each a hydrogen atom and at least partially together are ethylene, $R_4$, m and A are as defined for formula I, and n is an average number from 1 to 200, preferably from 1 to 20, most preferably from 1 to 10.

Compounds of formula IV, wherein p is the average number 1, and q is 0, may conveniently be prepared by reacting 2 mol of a compound of formula V with 3 mol of cyclopentadiene in known manner.

Compounds of formula IV, wherein p is an average number from 2 to 100 and q is 0, can be prepared by reacting (p+1) mol of a compound of formula V with (p+2) mol of cyclopentadiene in known manner.

Compounds of formula IV, wherein q is an average number from 1 to 100, can be prepared by reacting a compound of formula VI

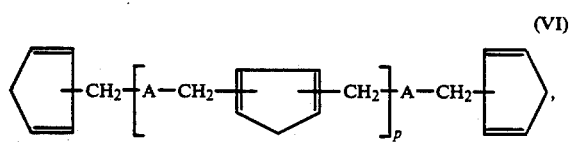

(VI)

wherein A and p are as defined for formula II, with a compound of formula III, wherein n has the meaning of q in formula II, in the temperature range from 50° to 100° C., by means of a Diels-Alder reaction.

Compounds of formula IV, wherein $R_1$ and $R_1'$ as well as $R_2$ and $R_2'$ are not only hydrogen, but together are also ethylene, and $R_4$, m, p, q and A are as defined for formula I, have not yet been described in the literature and therefore also constitute an object of the invention.

The invention therefore also relates to mixtures of compounds of formula IV, wherein $R_1$ and $R_1'$ as well as $R_2$ and $R_2'$ are each a hydrogen atom and at least partially together are ethylene, $R_3$ and $R_3'$ are each a hydrogen atom, A is as defined for formula II, and p and q are each an average number 1 to 100, preferably from 1 to 20, most preferably from 1 to 10.

The compounds of formula V are known and some are commercially available, for example p-xylylene dichloride or bis(chloromethyl) biphenyl. Aromatic bis(chloromethyl) compounds can also be prepared in simple manner by chloromethylation. The introduction of the chloromethyl group into the aromatic nucleus is effected in known manner with formaldehyde and hydrogen chloride in the presence of zinc chloride, aluminium chloride or phosphoric acid as catalyst by the Blanc reaction.

The compounds of formula VI are also known compounds and can be prepared in known manner by reacting compounds of formula V with cyclopentadiene.

The preparation of the spiro[2,4]hepta-4,6-dienes starting from bis(chloromethyl)benzene (p-xylylene dichloride) may be illustrated by means of the following simplified reaction scheme, bearing in mind that the reaction of bis(cyclopentadienyl) xylene with 1,2-dichloroethane leads not only to the monomeric bis(-spiro[2,4]hepta-4,6-dienyl) xylene, but also to a mixture in which, depending on the reaction conditions, usually up to 10% by weight of oligomeric spiro compounds may be present.

Reaction scheme:

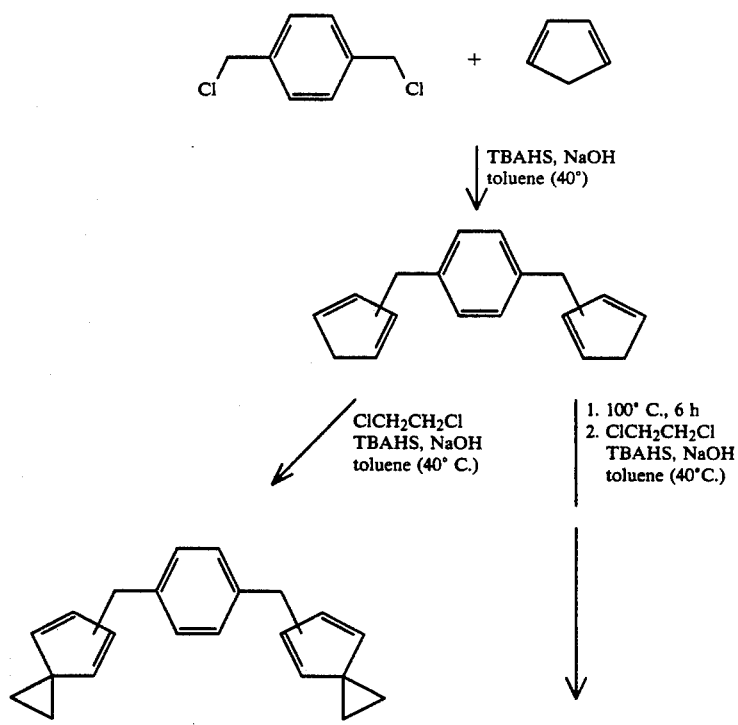

Reaction scheme:

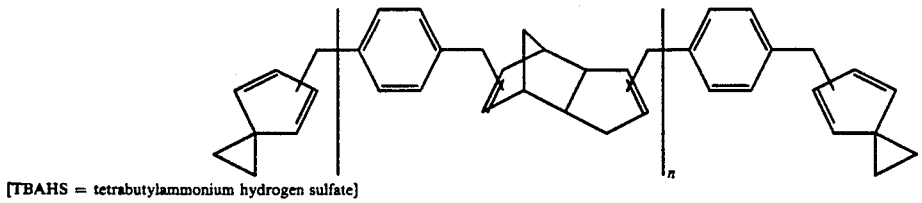

[TBAHS = tetrabutylammonium hydrogen sulfate]

Reaction of the mono(β-chloroethyl) cyclopentadienyl compound of formula

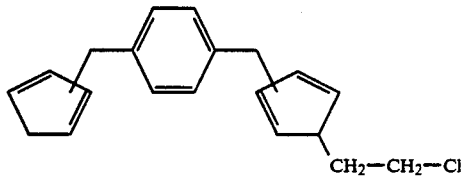

obtained as intermediate in the reaction of bis(cyclopentadienyl) xylene with 1,2-dichloroethane with another bis(cyclopentadienyl) xylene may lead to the formation of by-products of formula

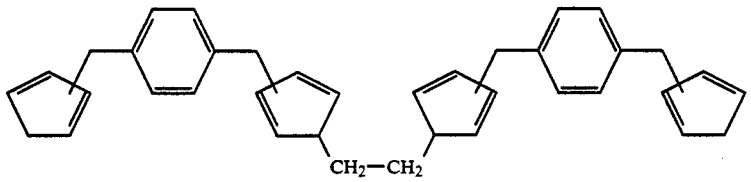

which, however, are present in only minor amounts in the novel mixtures. Similar by-products may also be formed by reacting the above intermediate with cyclopentadiene.

Replacing 1,2-dichloroethane with 1,4-dichlorobut-2-ene in the above reaction scheme leads under the same reaction conditions to the formation of a monomer and oligomeric vinyl-substituted spiro[2,4]hepta-4,6-dienes of the following formulae:

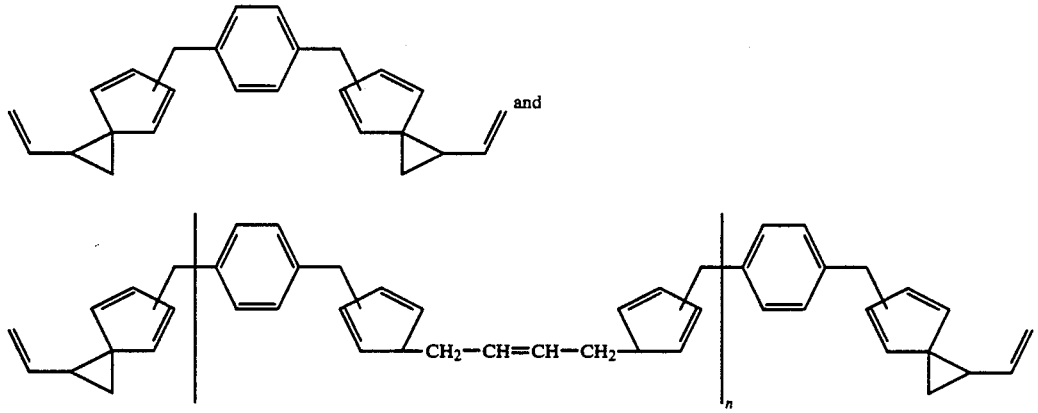

Suitable phase transfer catalysts which may be used in the preparation of the novel compounds include quaternary ammonium salts, such as tetramethylammonium chloride, tetraethylammonium chloride, benzyltrimethylammonium chloride, benzyltrimethylammonium acetate, methyltriethylammonium chloride, tetrabutylammonium chloride, methyl tri-$C_8$-$C_{10}$alkylammonium chlorides (Adogen®464) or tetrabutylammonium sulfate, quaternary ammonium bases, such as benzyltrimethylammonium hydroxide, as well as the crown ethers, suitably 12-crown-4-ether (1,4,7,10-tetraoxacyclododecane), 15-crown-5-ether (1,4,7,10,13-pentaoxacyclopentadecane), 18-crown-6-ether, dibenzo-18-crown-6-ether, dibenzo-24-crown-8-ether, dibenzo-1,4-dioxa-8,12-diazacyclopentadecy-5-14-diene, dicyclohexano-18-crown-6-ether or dicyclohexano-24-crown-8-ether.

The quaternary ammonium compounds and the cited crown ethers are known compounds, some of which are commercially available.

The preparation of the novel compounds is preferably carried out in the presence of an alkali solution, typically an aqueous solution of potassium or sodium hydroxide. As a rule a 30 to 80% aqueous alkali solution is used, preferably a 40 to 60% aqueous solution of sodium hydroxide.

The novel compounds can be cured by heating to elevated temperature to give insoluble and infusible resin products with a versatile range of technical applications. Suitable curing temperatures are ordinarily in the range from c. 130°–280° C., preferably 170°–250° C., the time taken depending very greatly on the curing temperature.

For many technical uses the addition of a curing catalyst is advantageous for the cure. For example, it is suitable to add a minor amount of a peroxide, whereby gelation times of a few minutes can be achieved at 200° C. Suitable peroxides are di-tert-butyl peroxide, di-tert-butyl peroxide butane, dilauryl peroxide, dicoumyl peroxide and tert-butylcoumyl peroxide in a concentration of 0.01 to 5%, preferably 0.25 to 0.5%, based on the weight of the novel compounds.

It is, however, also possible to use other known curing catalysts, typically cobalt naphthenate. Also suitable are the radical- or cation-forming catalysts, suitably the onium salts, preferably the araliphatic sulfonium salts, which are described in EP-A-0 379 464.

The term "curing" as used herein means the conversion of the novel compounds into crosslinked, insoluble and infusible products.

The preparation of the crosslinked infusible products is normally effected while simultaneously shaping to castings, laminates, compression mouldings, bonds or coatings, such as surface coatings.

The novel mixtures can be cured in the unfilled state or together with the additives or modifiers customarily used in plastics technology, including fillers, plasticisers, solvents, pigments, dyes, mould release agents, flame retardants and the like, with shaping, after incorporation in adhesive joints or as flat structures, with or without the application of pressure. The invention also relates to the moulded articles or flat structures fabricated from the novel mixtures by curing.

The flame retardant compounds used in the novel mixtures are preferably phosphorus-containing compounds of formula VII

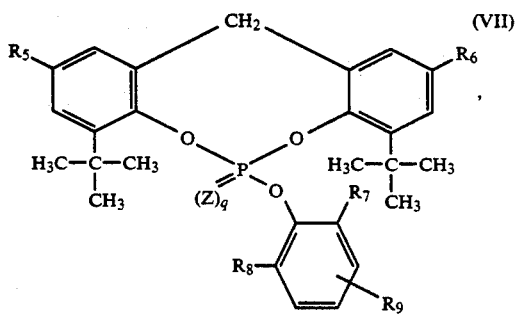

wherein $R_5$ and $R_6$ are each independently of the other hydrogen, $C_1$–$C_6$alkyl, phenyl or naphthyl, each unsubstituted or substituted by 1 to 3 $C_1$–$C_4$alkyl groups, $R_7$ and $R_8$ are each independently of the other hydrogen or $C_1$–$C_4$alkyl, with the proviso that $R_7$ and $R_8$ may not simultaneously be hydrogen, $R_9$ is hydrogen, $C_1$–$C_6$alkyl, phenyl or naphthyl, each unsubstituted or substituted by 1 to 3 $C_1$–$C_4$alkyl groups, Z is oxygen or sulfur, and q is 0 or 1.

The compounds of formula VII and the use thereof are disclosed in EP-A-0 412 936 and can be prepared by the process described therein.

The novel mixtures are preferably used for making laminates, as they have very good adhesion to metals, especially copper, and they also can be used by conventional techniques for the fabrication of copper-clad boards. The resins obtained by curing from the novel mixtures have good dielectrical properties, which make the resins especially suitable for producing copper-clad laminates as base material for printed circuit boards.

The novel compounds can also be used for making thin films for printed wiring boards with high density circuit patterns, as in the microchips industry (multichip modulus technology).

The quotient of the two molecular weight values Mw/Mn may be regarded as an indicator of the magnitude of the molecular weight distribution. In a homogeneous compound, the quotient is 1 and in polymers it is always >1.

EXAMPLE 1

Spiro[2,4]hepta-4,6-dienes based on p-xylylene dichloride 87.5 g (0.5 mol) of p-xylylene dichloride are dissolved in 750 g of toluene under a stream of $N_2$ in a sulfonation flask fitted with mechanical stirrer, reflux condenser, thermometer and two dropping funnels. Then 3.4 g (0.01 mol) of tetrabutylammonium hydrogen sulfate (TBAHS) are added and the mixture is warmed to 35° C. With rapid stirring, 69.4 g (1.05 mol) of freshly distilled cyclopentadiene and 320 g of a 50% solution of NaOH (4 mol) are simultaneously added dropwise so that the temperature is kept at 30° C. The mixture is stirred for 2 hours (h) at 35° C., heated for 1 h at 50° C., and then cooled to 35° C. At this temperature 10.2 g (0.03 mol) of TBAHS are added. Afterwards 98.9 g (1 mol) of 1,2-dichloroethane and 194 g of a 50% solution of NaOH (2.42 mol) are simultaneously added dropwise. The mixture is stirred for 1 h at 35° C. and for 5.5 h at 50° C. and then cooled to room temperature (RT). The aqueous phase is separated, and the organic phase is acidified to pH=4 with 510 g of a 30% solution of $NaHSO_4$ and washed twice with water. The aqueous phase is separated and the organic phase is dried over sodium sulfate and then filtered. The toluene is removed by evaporation. Yield: 99.2 g (70% of theory) of a mixture of oligomeric spiro[2,4]hepta-4,6-dienes as a brown resin.

Elemental analysis: calcd C=92.26%; found C=90.82%; calcd H=7.74%; found H=7.53%.

Total chlorine content: found 0.97%.

$^1$H-NMR spectrum:

$$\frac{\text{H cyclopropyl}}{\text{H aromatic}} = 1.16 \text{ (theor. } = 2.0)$$

Gel permeation chromatography: (GPC) Mn=456; Mw=1039.

EXAMPLE 2

Spiro[2,4]hepta-4,6-dienes based on 4,4'-bis(chloromethyl) biphenyl 1.256 kg (5.0 mol) of bis(chloromethyl) biphenyl and 34 g (0.1 mol) of TBAHS are suspended in 7 kg of toluene at 35° C. under a stream of $N_2$ in a 12 liter reactor fitted with mechanical stirrer, reflux condenser, thermometer and two dropping funnels. With efficient stirring, 695 g (10.5 mol) of freshly distilled cyclopentadiene and 1.6 kg of a 50% solution of NaOH (20 mol) are simultaneously added dropwise to this suspension so that the temperature is kept between 35° and 38° C. The mixture is stirred for 1.5 h at 35° C. and then warmed to 40° C. At this temperature 102 g (0.3 mol) of TBAHS and 990 g (10 mol) of 1,2-dichloroethane are added rapidly, and then 1.928 kg of a 50% solution of NaOH (24.1 mol) are added dropwise over 0.5 h. The mixture is stirred for 1 h at 40° C. and for 2 h at 50° C., and then cooled to room temperature. After addition of 0.5 kg of water, the aqueous phase is decanted and separated. The organic phase is acidified to pH=4 with 0.1 kg of a 40% solution of NaHSO$_4$. The aqueous phase is separated and the organic phase is dried over sodium sulfate and then filtered over kieselgur. The toluene is removed by evaporation. Yield: 1.274 kg (78.5% of theory) of a mixture of oligomeric spiro[2,4]hepta-4,6-dienes as a brown resin.

Elemental analysis: calcd C=92.77%; found C=92.00%; calcd H=7.23%; found H=7.1%.

Total chlorine content: found 0.169%.

Hydrolisable chlorine: found 0.024%.

$^1$H-NMR spectrum:

$$\frac{\text{H cyclopropyl}}{\text{H aromatic}} = 0.39 \text{ (theory = 1.0)}$$

GPC: Mn=544; Mw=1385.

EXAMPLE 3

43.75 g (0.25 mol) of p-xylylene dichloride, 1.7 g (0.005 mol) of TBAHS and 375 g of toluene are placed in a 2.5 liter 5-neck flask fitted with a high-speed stirrer, N$_2$ gas inlet, thermometer, reflux condenser and two dropping funnels. Then 34.7 g (0.525 mol) of cyclopentadiene are placed in one dropping funnel and 160 g (2.00 mol) of 50% aqueous sodium hydroxide are placed in the other. With rapid stirring and under a continuous stream of N$_2$ gas, the cyclopentadiene and the sodium hydroxide solution are simultaneously added dropwise to the flask over while keeping the temperature of the reaction solution at 25° C. by external cooling. The solution is then stirred for 2.5 h at 25° C. and thereafter for 1.5 h at 50° C. The solution is then cooled to 25° C.

The reaction mixture is then subjected to the Diels-Alder reaction by heating it for 6 h to 100° C. The reaction solution is thereafter cooled to RT. To this solution are added 5.09 g (0.015 mol) of TBAHS and 97 g of a 50% aqueous solution of sodium hydroxide. Under a N$_2$ atmosphere, 49.3 g (0.5 mol) of 1,2-dichloroethane are added dropwise continuously over 30 minutes, while keeping the temperature of the reaction solution at 34°–40° C. by external cooling. Afterwards the reaction solution is kept for another 6 h at 50° C., then cooled to room temperature and neutralised with 800 g of NaHSO$_4$. The organic phase is separated from the aqueous phase, washed twice with 200 ml of water and then dried over anhydrous Na$_2$SO$_4$. The toluene is removed from the dried toluene solution under vacuum at RT on a rotary evaporator, and the residual resin is subjected for 15 minutes to a high vacuum to remove residual volatile matter. The yield is 65% of theory of polymeric spiro[2,4]hepta-4,6-dienes as a brown resin.

Elemental analysis: calcd C=92.26%; found C=89.98%; calcd H=7.74%; found H=7.66%.

Total chlorine content: found 0.54%

GPC: Mn=1172 Mw=7448.

$^1$H-NMR spectrum:

$$\frac{\text{H cyclopropyl}}{\text{H aromatic}} = 0.92$$

Viscosity at 100° C.=44,875 mPa.s.

EXAMPLE 4

The resin obtained in Example 3 is processed to mouldings by heating it in moulds for 6 h at 150° C., for 3 h at 180° C. and for 3 h at 220° C. The mouldings have the following properties:

| | |
|---|---|
| T$_G$ (TMA) | = 289° C. |
| heat distortion (ISO-R 75) | = 216° C. |
| flexural strength (ISO-R 178) | = 92.6 N/mm$^2$ |
| flexural elongation (DIN 53 371) | = 3.0% |
| flexural modulus (DIN 53 371) | = 3111 N/mm$^2$ |
| weight loss (temperature gravimetry = TGA) | = 0.5% at 310° C. |
| | = 1.0% at 347° C. |
| | = 5.0% at 417° C. |
| water absorption | = 0.115% after 24 h immersion at 23° C. |
| | = 0.134% after 30 min immersion at 100° C. |
| dielectric constant | = 2.6–2.7 (3 KHz at 24° C.) |
| dielectric constant after exposure to moisture for 800 h at 85° C. and 85% relative humidity | = 2.7–2.8 (3 KHz at 24° C.) |
| dielectric loss factor tan δ | = <0.005 (100 Hz-1 MHz) |

EXAMPLE 5

The resin obtained in Example 2 is processed to mouldings by heating it in moulds for 6 h at 150° C., for 3 h at 180° C. and for 3 h at 220° C. The mouldings have the following properties:

| | |
|---|---|
| water absorption | = 0.246–0.276% after 22 h immersion at 25° C. |
| | = 0.825–0.839% after 1140 h immersion at 25° C. |
| dielectric constant | = 2.83 (3 KHz at 25° C.) |
| dielectric constant after exposure to moisture for 1400 h at 85° C. and 85% relative humidity | = 2.92–2.96 (3 KHz at 24° C.). |

EXAMPLE 6

Vinylspiro[2,4]heptadienes based on p-xylylene dichloride and 1,4-dichlorobut-2-ene 35 g (0.2 mol) of p-xylylene dichloride are dissolved in 300 g of toluene under a stream of N$_2$ in a sulfonation flask fitted with mechanical stirrer, reflux condenser, thermometer and two dropping funnels. Then 1.35 g (0.004 mol) of TBAHS are added and the mixture is warmed to 35° C. With efficient stirring, 29.1 g (0.44 mol) of freshly distilled cyclopentadiene and 129 g (1.6 mol) of a 50% solution of sodium hydroxide are simultaneously added dropwise so that the temperature is kept between 35° and 40° C. The mixture is stirred for 2 h at 35° C. and overnight at RT. The mixture is then filtered and the organic phase is separated.

128 g (1.6 mol) of a 50% NaOH solution, 6.79 g (0.02 mol) of TBAHS and 160 g of toluene are placed in a sulfonation flask fitted as above and the mixture is warmed to 30° C. under a stream of N$_2$. With efficient stirring, 50 g (0.4 mol) of 1,4-dichlorobut-2-ene and the organic phase obtained in the first phase are simultaneously added dropwise to the above mixture so that the reaction temperature is kept between 30° and 35° C. The mixture is stirred for 1 h at this temperature and then heated for 1 h to 50° C. The mixture is then cooled to RT and filtered, and the aqueous phase is separated.

The organic phase is acidified to pH=4 with a 30% solution of NaHSO$_4$ and washed twice with water. It is dried over sodium sulfate and filtered, and the toluene is then removed by evaporation. Yield: 53 g (78% of theory) of a brown resin.

Elemental analysis: calcd C=92.26%; found C=90.35%; calcd H=7.74%; found H=7.56%.
Total chlorine content: found 0.169%.
Hydrolisable chlorine: found 1.045%.
$^1$H-NMR spectrum:

$$\frac{\text{H cyclopropyl}}{\text{H aromatic}} = 0.6 \text{ (theory = 1.5)}$$

GPC: Mn=706; Mw=5762.

EXAMPLE 7

31 g of a compound of formula VII, wherein R$_5$, R$_6$, R$_7$ and R$_8$ are each methyl, R$_9$ is hydrogen, and q is 0 (phosphorus additive A) and 31 g of a compound of formula VII, wherein R$_5$, R$_6$, R$_7$ and R$_8$ are each methyl, R$_9$ is hydrogen, q is 1 and Z is an oxygen atom (phosphorus additive B) are added to 500 g of a 62% solution of the compound obtained in Example 2 in toluene. The mixtures are stirred until the phosphorus additives are completely dissolved. The toluene is then distilled off under vacuum at 50° C./30 mbar on a rotary evaporator, and the clear viscous resin solution is subjected to a vacuum of 0.1 mbar for 3 minutes at 120° C. and for 1 minute at 150° C. The viscous resin solution is poured into 4 mm thick aluminum moulds which have been preheated to 150° C., and cured for 3 h at 150° C., for 3 h at 180° C. and for 3 h at 220° C. and postcured for 6 h at 200° C. The specimens obtained are dried for 7 days at 70° C. before being subjected to the UL 94 (Underwriter's Laboratories) flame-resistance test. The specimens of the resin made flame-resistant with the phosphorus additives A and B each have the value VO. In addition, the dielectric constant of the specimens which contain phosphorus additive A is measured before and after immersion in water, as is also the water absorption.

| | |
|---|---|
| Dielectric constant, dry | = 2.9 (3 KHz at 25° C.) |
| dielectric constant, after 24 h immersion in water at 100° C. | = 3.0 (3 KHz at 25° C.) |
| water absorption after 24 h immersion at 100° C. | = 0.39% |

What is claimed is:

1. A mixture essentially comprising compounds of formula I or II

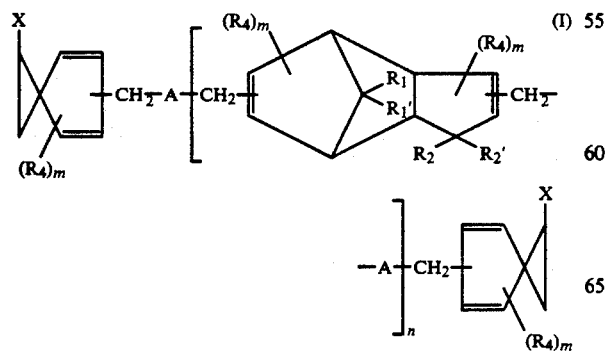

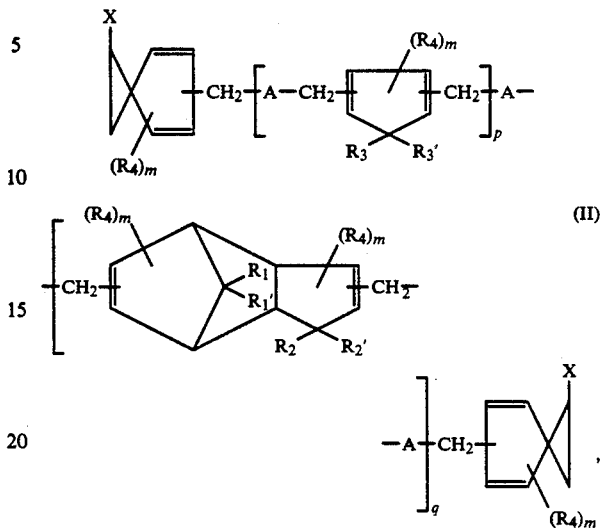

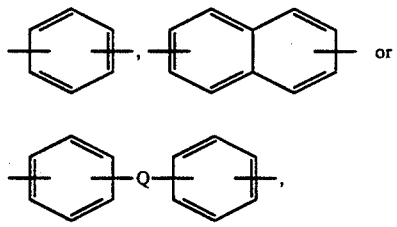

wherein X is a hydrogen atom or vinyl, A is a divalent aromatic radical which is unsubstituted or substituted by one or more C$_1$–C$_{20}$alkyl groups, halogen atoms or halogen-substituted C$_1$–C$_{20}$alkyl groups, R$_1$, R$_1'$, R$_2$, R$_2'$, R$_3$ and R$_3'$ are each a hydrogen atom, or R$_1$ and R$_1'$, R$_2$ and R$_2'$ and R$_3$ and R$_3'$ are each together ethylene, R$_4$ is C$_1$–C$_6$alkyl, phenylalkyl containing 1 to 6 carbon atoms in the alkyl moiety or is trialkylsilyl containing 1 to 6 carbon atoms in each alkyl moiety, m is 0, 1 or 2, n is 0 or an average number from 1 to 200, p is an average number from 1 to 100 and q is 0 or an average number from 1 to 100.

2. A mixture essentially comprising compounds of formula I or II, wherein X is a hydrogen atom, and A, R$_1$, R$_1'$, R$_2$, R$_2'$, R$_4$, m and n are as defined in claim 1.

3. A mixture essentially comprising compounds of formula I, wherein A, R$_1$, R$_1'$, R$_2$, R$_2'$, R$_4$, m and n are as defined in claim 1.

4. A mixture according to claim 1, wherein A is an unsubstituted or a C$_1$–C$_4$-alkyl-substituted radical of formula

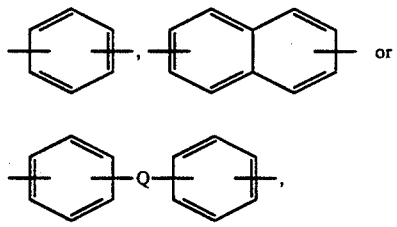

wherein Q is a direct bond, —(CH$_2$)$_r$—, —C(CH$_3$)$_2$—, —O—, —CO—, —S— or —SO$_2$—, where r is a number from 1 to 12, R$_1$, R$_1'$, R$_2$ and R$_2'$ are as defined in claim 1, m is 0, 1 or 2, and R$_4$ is methyl or ethyl, and n is 0 or an average number from 1 to 20.

5. A mixture comprising compounds of formula I according to claim 1, wherein A is phenylene or biphenylene, R$_1$, R$_1'$, R$_2$ and R$_2'$ are as defined in claim 1, and n is 0 or an average number from 1 to 20.

6. A mixture according to claim 5, wherein n is 0 or an average number from 1 to 10.

7. A process for the preparation of a mixture as claimed in claim 1, which comprises reacting compounds of formula III or IV

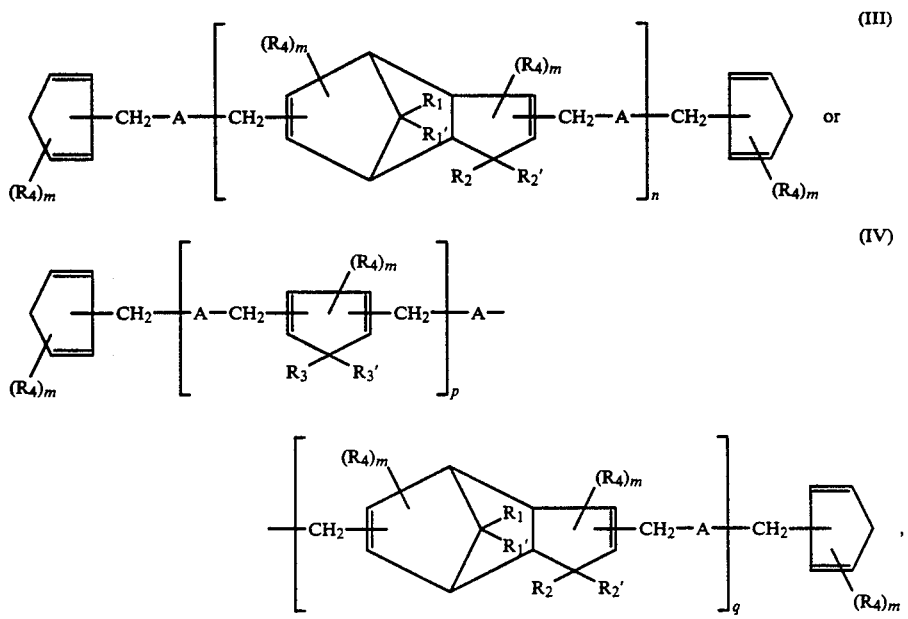

wherein A, $R_1$, $R_1'$, $R_2$, $R_2'$, $R_3$, $R_3'$, $R_4$, m, n, p and q are as defined for formulae I and II in claim 1, with 1,2-dichloroethane, 1,2-dibromoethane, 1,4-dichloro- or 1,4-dibromobut-2-ene in the presence of a phase transfer catalyst and of alkali and in the temperature range from 20° to 50° C., using at least 0.1 mol of 1,2-dichloroethane, 1,2-dibromoethane, 1,4-dichloro- or 1,4-dibromobut-2-ene per 1 mol of compound of formula III or IV.

8. A process according to claim 7, which comprises using at least 2 mol of 1,2-dichloroethane, 1,2-dibromethane, 1,4-dichloro- or 1,4-dibromobut-2-ene per 1 mol of compound of formula III or IV.

* * * * *